(12) United States Patent
Harada et al.

(10) Patent No.: US 8,274,243 B2
(45) Date of Patent: Sep. 25, 2012

(54) PARTICLE BEAM TREATMENT APPARATUS AND RESPIRATION NAVIGATION APPARATUS USED THEREFOR

(75) Inventors: Hisashi Harada, Tokyo (JP); Akihiko Hoshi, Tokyo (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 353 days.

(21) Appl. No.: 12/682,012

(22) PCT Filed: Jun. 9, 2008

(86) PCT No.: PCT/JP2008/060553
§ 371 (c)(1),
(2), (4) Date: Apr. 7, 2010

(87) PCT Pub. No.: WO2009/150708
PCT Pub. Date: Dec. 17, 2009

(65) Prior Publication Data
US 2010/0207042 A1    Aug. 19, 2010

(51) Int. Cl.
*H01J 23/00* (2006.01)
(52) U.S. Cl. ............ 315/500; 315/504; 250/505.1
(58) Field of Classification Search ......... 250/492.3; 315/500; 378/65; 482/13
See application file for complete search history.

(56) References Cited

U.S. PATENT DOCUMENTS

| | | | |
|---|---|---|---|
| 5,949,080 A * | 9/1999 | Ueda et al. ............ | 250/492.3 |
| 6,106,481 A | 8/2000 | Cohen | |
| 7,122,978 B2 * | 10/2006 | Nakanishi et al. ......... | 315/500 |
| 2005/0119560 A1 | 6/2005 | Mostafavi | |
| 2005/0231138 A1 * | 10/2005 | Nakanishi et al. ......... | 315/500 |
| 2007/0211857 A1 * | 9/2007 | Urano et al. ............ | 378/65 |
| 2008/0317204 A1 * | 12/2008 | Sumanaweera et al. ...... | 378/65 |
| 2009/0170664 A1 * | 7/2009 | Shirasaki et al. ......... | 482/13 |

FOREIGN PATENT DOCUMENTS

| | | |
|---|---|---|
| JP | 03-111033 A | 5/1991 |
| JP | 07-303710 A | 11/1995 |
| JP | 2001-518330 A | 10/2001 |
| JP | 2002-360543 A | 12/2002 |
| JP | 2003-033443 A | 2/2003 |
| JP | 2007-042659 A | 2/2007 |
| JP | 2007-190278 A | 8/2007 |
| JP | 2007-236760 A | 9/2007 |
| JP | 2008-071494 A | 3/2008 |
| JP | 2008-119449 A | 5/2008 |
| JP | 2008-514371 A | 5/2008 |

OTHER PUBLICATIONS

International Search Report (PCT/ISA/210) for PCT/JP2008/060553 dated Jul. 22, 2008.

\* cited by examiner

*Primary Examiner* — Nikita Wells
*Assistant Examiner* — Johnnie L Smith
(74) *Attorney, Agent, or Firm* — Buchanan Ingersoll & Rooney PC

(57) ABSTRACT

Target respiration information is created in which a patient respiration pattern is set in advance to a cycle suitable for an operation cycle of a synchrotron, and the target respiration information is informed to the patient, so that a patient respiration timing becomes a state suitable for an operation of the synchrotron in such a manner that the patient consciously matches with the informed information.

10 Claims, 5 Drawing Sheets

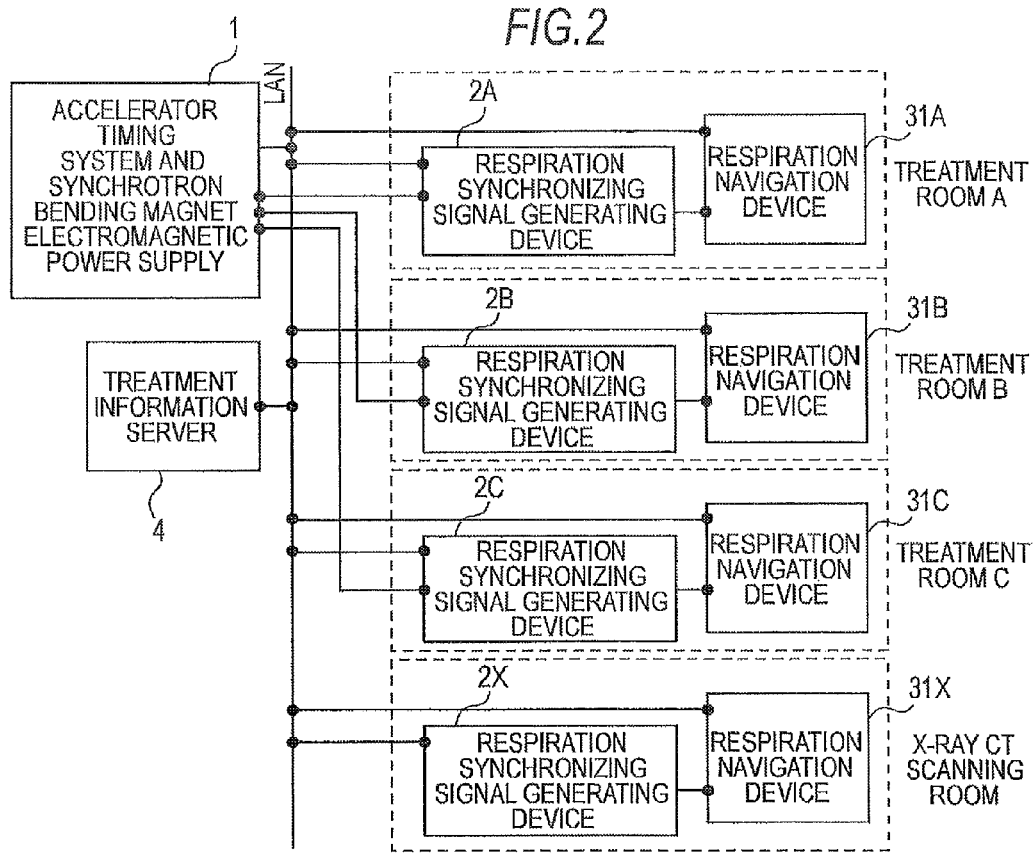
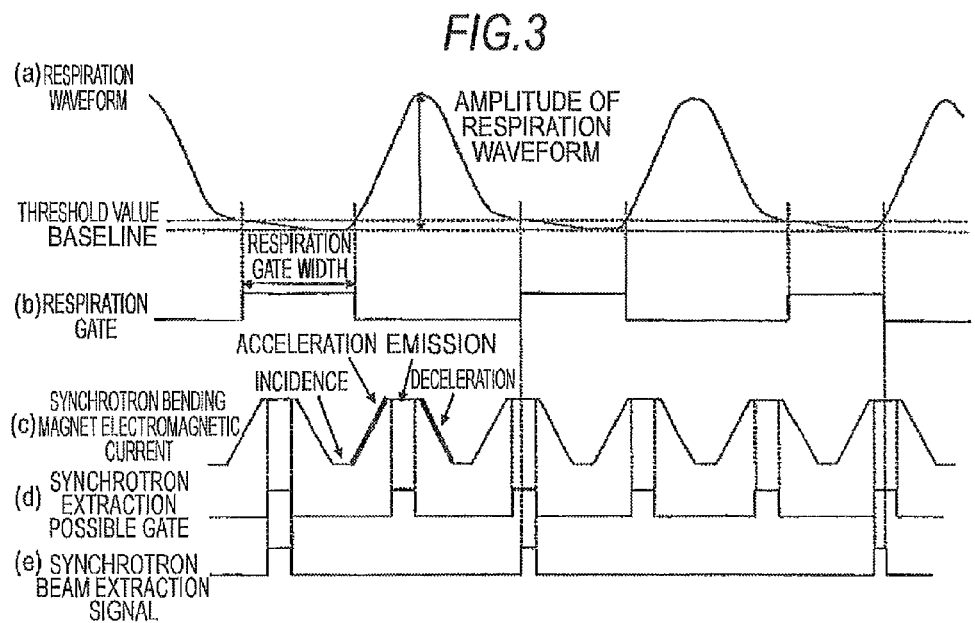

FIG.6

TABLE 1
EXAMPLE OF SETTING PARAMETER OF TARGET RESPIRATION INFORMATION:
CASE OF PERFORMING ONE-TIME IRRADIATION FOR EACH RESPIRATION CYCLE

1) ACCELERATOR PARAMETER A

| SYNCHROTRON CYCLE | 2.0 SECONDS |
|---|---|
| SPILL TIME | 0.4 SECONDS |

TARGET RESPIRATION INFORMATION

|  | CASE (1) | CASE (2) | CASE (3) |
|---|---|---|---|
| TARGET RESPIRATION CYCLE | 4.0 SECONDS | 6.0 SECONDS | 8.0 SECONDS |
| TARGET RESPIRATION GATE | 0.4 SECONDS OR MORE | 0.4 SECONDS OR MORE | 0.4 SECONDS OR MORE |
| RESPIRATION GATE EFFICIENCY | 0.1 OR MORE | 0.0667 OR MORE | 0.05 OR MORE |
| IRRADIATION EFFICIENCY | 0.5 | 0.333 | 0.25 |

2) ACCELERATOR PARAMETER B

| SYNCHROTRON CYCLE | 1.6 SECONDS |
|---|---|
| SPILL TIME | 0.8 SECONDS |

TARGET RESPIRATION INFORMATION

|  | CASE (4) | CASE (5) | CASE (6) |
|---|---|---|---|
| TARGET RESPIRATION CYCLE | 3.2 SECONDS | 4.8 SECONDS | 6.4 SECONDS |
| TARGET RESPIRATION GATE | 0.8 SECONDS OR MORE | 0.8 SECONDS OR MORE | 0.8 SECONDS OR MORE |
| RESPIRATION GATE EFFICIENCY | 0.25 OR MORE | 0.1667 OR MORE | 0.125 OR MORE |
| IRRADIATION EFFICIENCY | 0.5 | 0.333 | 0.25 |

FIG.7

TABLE 2
EXAMPLE OF SETTING PARAMETER OF TARGET RESPIRATION INFORMATION:
CASE OF PERFORMING TWO-TIME IRRADIATION FOR EACH RESPIRATION CYCLE

1) ACCELERATOR PARAMETER A

| SYNCHROTRON CYCLE | 2.0 SECONDS |
|---|---|
| SPILL TIME | 0.4 SECONDS |

TARGET RESPIRATION INFORMATION

|  | CASE (7) | CASE (8) | CASE (9) |
|---|---|---|---|
| TARGET RESPIRATION CYCLE | 4.0 SECONDS | 6.0 SECONDS | 8.0 SECONDS |
| TARGET RESPIRATION GATE | 2.4 SECONDS OR MORE | 2.4 SECONDS OR MORE | 2.4 SECONDS OR MORE |
| RESPIRATION GATE EFFICIENCY | 0.6 OR MORE | 0.4 OR MORE | 0.3 OR MORE |
| IRRADIATION EFFICIENCY | 1 | 0.667 | 0.5 |

2) ACCELERATOR PARAMETER B

| SYNCHROTRON CYCLE | 1.6 SECONDS |
|---|---|
| SPILL TIME | 0.8 SECONDS |

TARGET RESPIRATION INFORMATION

|  | CASE (10) | CASE (11) | CASE (12) |
|---|---|---|---|
| TARGET RESPIRATION CYCLE | 3.2 SECONDS | 4.8 SECONDS | 6.4 SECONDS |
| TARGET RESPIRATION GATE | 2.4 SECONDS OR MORE | 2.4 SECONDS OR MORE | 2.4 SECONDS OR MORE |
| RESPIRATION GATE EFFICIENCY | 0.75 | 0.5 | 0.375 |
| IRRADIATION EFFICIENCY | 1 | 0.667 | 0.5 |

PARTICLE BEAM TREATMENT APPARATUS AND RESPIRATION NAVIGATION APPARATUS USED THEREFOR

TECHNICAL FIELD

The present invention relates to a particle beam treatment apparatus such as a particle beam cancer treatment apparatus.

BACKGROUND ART

For example, when a radiation treatment apparatus such as a cancer treatment apparatus is used, a countermeasure has been demanded for a case in which a position or a shape of a patient target diseased portion is changed due to a patient physiological phenomenon. Particularly, when the target diseased portion is a chest or an abdomen, a variation in the position or shape of the target diseased portion causes deterioration in treatment or diagnosis precision, and sometimes the patient may be necessarily exposed to radiation.

In general, a particle beam treatment apparatus includes a particle beam generating unit such as a synchrotron, a particle beam irradiation unit which allows a patient to be irradiated with a particle beam generated from the particle beam generating unit through a particle beam transport system, a respiration signal processing unit which determines whether a respiration phase is in a state where irradiation is possible on the basis of a temporal variation of a respiration signal obtained from a patient respiration measurement device, a control unit which controls the particle beam generating unit or the particle beam irradiation unit, and the like.

In addition, in the case where irradiation treatment is performed on a portion such as a lung or a liver moving in accordance with respiration, patient respiration is guided so as to be easily synchronized with a particle beam irradiation timing by changing target respiration information, so that the irradiation is performed when a position and a shape of a diseased portion are substantially constant (for example, refer to Patent Document 1).

Patent Document 1: JP-A-2003-33443 (refer to FIGS. 1 and 7)

DISCLOSURE OF THE INVENTION

Problems that the Invention is to Solve

However, in the patient respiration guiding method disclosed in Patent Document 1, since a final waveform of the target respiration information is not informed to the patient, and the respiration is performed in accordance with the changing target respiration information at each time, it is difficult for the patient to know the final target waveform, and hence there are problems in that it is difficult to synchronize with an original particle beam irradiation timing of the synchrotron, and to realize a highly efficient apparatus.

An object of the invention is to solve such a problem, and to provide a particle beam treatment apparatus capable of efficiently performing irradiation of a particle beam in such a manner that fixed target respiration information set in accordance with an irradiation cycle of a synchrotron is informed in advance to a patient, which assists in matching a patient respiration cycle.

Means for Solving the Problems

According to the invention, there is provided a respiration navigation apparatus used for a particle beam treatment apparatus including an accelerator operated on the basis of predetermined operation timing information, the respiration navigation apparatus comprising a respiration navigation computer which stores target respiration information having a cycle set in advance on the basis of the operation timing information, and a respiration information informing device which informs a patient of distinct past and future portions of a respiration waveform obtained by quantifying information, involved with a respiration amplitude of the target respiration information, in time series.

According to an other aspect of the invention, there is provided a particle beam treatment apparatus comprising a particle beam generating device which includes an accelerator operated on the basis of predetermined operation timing information and generates a particle beam; a patient respiration measurement device which measures a patient respiration state;

a respiration synchronizing device which allows a patient to be irradiated with the particle beam on the basis of the patient respiration state information measured by the patient respiration measurement device; a respiration navigation computer which stores target respiration information having a cycle set in advance on the basis of the operation timing information; and a respiration information informing device which informs the patient of distinct past and future portions of a respiration waveform obtained by quantifying information, involved with a respiration amplitude of the target respiration information, in time series.

Advantage of the Invention

When the patient consciously matches with the target respiration information, there arises a state in which the respiration is stable and is suitable for the operation cycle of the synchrotron, and hence operation efficiency is improved. Accordingly, since the timing increases at which the respiration gate signal overlaps with the emission possible signal of the synchrotron, the irradiation treatment time is shortened.

BRIEF DESCRIPTION OF THE DRAWINGS

FIG. 2 is a configuration diagram of an arrangement in the case where the invention is applied to plural treatment rooms and an X-ray CT room.

FIG. 3 is a waveform diagram of each unit of the particle beam treatment apparatus of the invention.

FIG. 6 is a table showing a setting example of a target respiration gate width and a target respiration cycle for operation parameters of two types of synchrotrons A and B, and shows a case in which one-time irradiation is performed for each respiration cycle.

FIG. 7 is a table showing a setting example of a respiration gate width of operation parameters A and B of two types of synchrotrons, and shows a case in which two-time irradiation is performed for each respiration cycle.

BEST MODE FOR CARRYING OUT THE INVENTION

Figure 1:
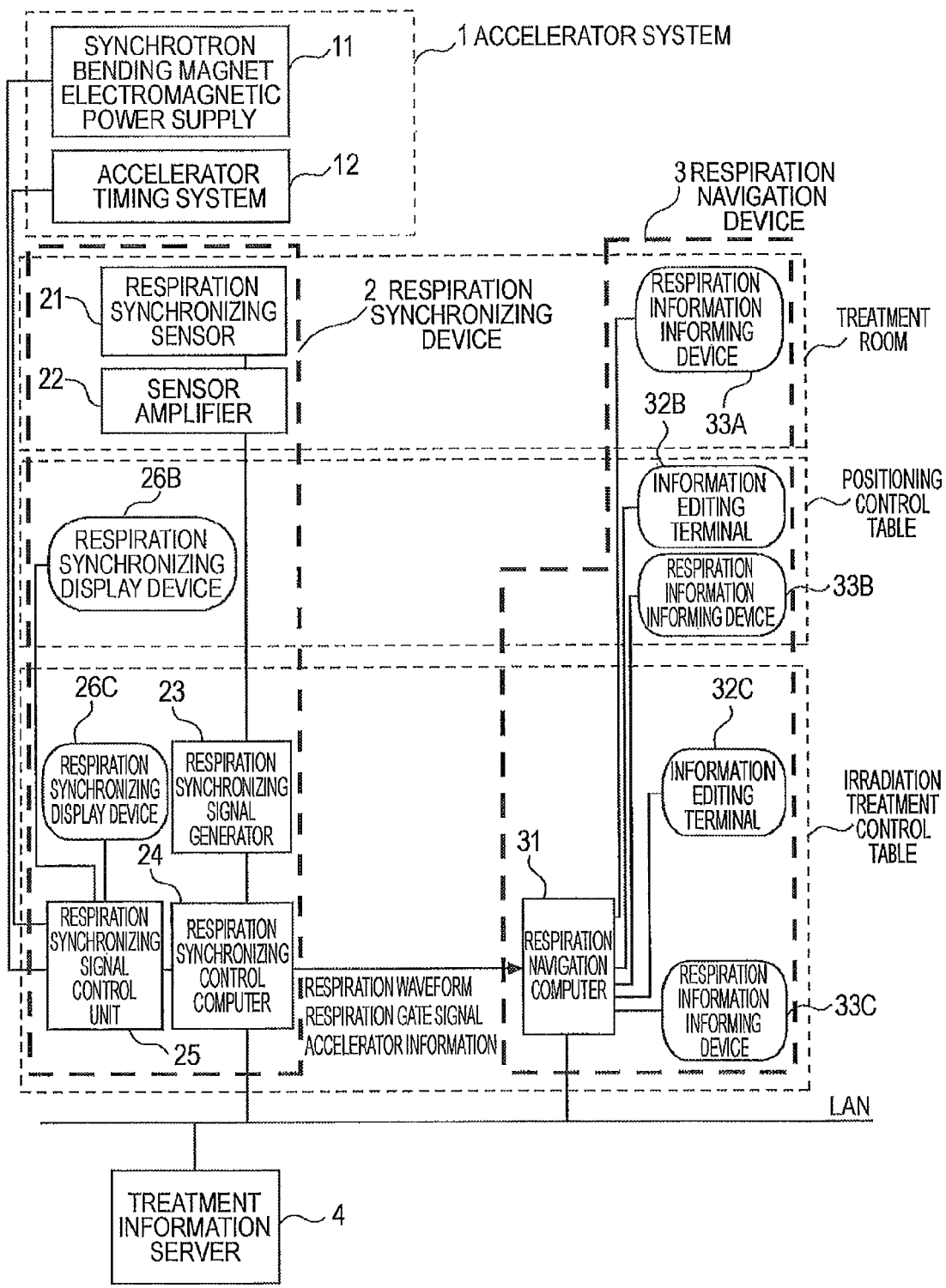
FIG. 1 is a main configuration diagram of a particle beam treatment apparatus of the invention.

An embodiment of a particle beam treatment apparatus of the invention will be described by using a main configuration diagram of FIG. 1. FIG. 1 shows one room (for example, A) of plural treatment rooms, and shows an example in which three operation spaces are provided such as a treatment room, a positioning control table, and a irradiation treatment control table. A treatment operator performs an operation by using any one of three spaces. In the drawing, 1 denotes an accelerator system such as a synchrotron which accelerates a particle beam and includes a synchrotron bending magnet electromagnetic power supply 11 or an accelerator timing system 12. 2 denotes a respiration synchronizing device which is provided in the treatment room with a respiration synchronizing sensor 21 as a patient respiration measurement device which detects a respiration state of a patient and a sensor amplifier 22 for converting and amplifying a signal from the sensor 21, where the positioning control table is provided with a respiration synchronizing display device 26B.

In addition, the irradiation treatment control table is provided with a respiration synchronizing signal generator 23 which processes the signal amplified by the sensor amplifier 22 and controls the output of the respiration synchronizing signal, a respiration synchronizing control computer 24 which sets a parameter during the operation of the respiration synchronizing signal generator 23 or a timing for generating a synchronizing signal, a respiration synchronizing signal control unit 25 which performs a signal conversion on a respiration waveform output from the signal generator 23 or a respiration synchronizing waveform output from the respiration synchronizing control computer 24 and distributes the resultant to the accelerator system 1 or the display device 26B, and a respiration synchronizing display device 26C which displays an operation state of the particle beam treatment apparatus and the respiration synchronizing signal for the operator.

3 denotes a respiration navigation device including a respiration navigation computer 31 to which a respiration waveform, a respiration gate signal, accelerator information, and the like are input from the respiration synchronizing control computer 24 and which performs a storage, a process, and a management thereof, information editing terminals 32B and 32C which edit or change information from the respiration navigation computer 31, and respiration information informing devices 33A, 33B, and 33C which informs the patient of information. 4 denotes a treatment information server which includes a computer, a sequencer, and the like and stores a patient treatment data. Information on the respiration navigation is managed while being stored in the treatment information server 4 together with the patient treatment data.

The respiration information informing device 33 or the information editing terminal 32 may be provided at plural positions. For example, the respiration information informing device is provided in the treatment room, the positioning operation table, and the irradiation treatment control table. In addition, since an operation of acquiring treatment plan information is performed in an X-ray CT scanning control room, the respiration information informing device may be also provided in the X-ray CT scanning control room. FIG. 2 shows a configuration example in the case where the present device is provided in the plural treatment rooms A, B, and C and the X-ray CT scanning room used before creating the treatment plan. The terminals are used by a person involved with a medical treatment, and are used to perform each of operations of acquiring, creating, and editing control data before the irradiation treatment and are used to adjust a respiration phase or to check a respiration synchronizing state during the irradiation treatment.

In addition, in the embodiment, a configuration is shown in which the respiration navigation computer is provided separately from the respiration synchronizing control computer so as to easily add other functions, but the respiration synchronizing control computer and the respiration navigation computer may be configured as one common computer. Further, the respiration synchronizing display device is provided separately from the respiration information informing device, but the functions described in the embodiment may be realized by switching one display device.

As a respiration measurement method using the respiration synchronizing sensor 21, there are several existing methods such as a method of detecting a movement of a patient abdominal portion by using a position sensitive detector for detecting a laser source attached to a patient abdominal portion and a method of measuring a temperature variation in the vicinity of a nasal cavity in accordance with a patient inhalation by using an image process through a thermistor or an infrared camera.

FIG. 3 is an operation waveform diagram of each unit of the particle beam treatment apparatus, where FIG. 3($a$) shows a respiration waveform, FIG. 3($b$) shows a respiration gate, FIG. 3($c$) shows a synchrotron bending magnet electromagnetic current, FIG. 3($d$) shows a synchrotron beam extraction possible gate, and FIG. 3($e$) schematically shows a timing of a synchrotron beam extraction signal.

As shown in the drawing, a threshold value is set for the respiration waveform (a) detected by the respiration synchronizing sensor 21, the respiration gate (b) is turned on when it is in a stable respiration state, and then the accelerator is instructed that an irradiation is possible using a respiration gate width (arrow).

The bending magnet electromagnetic current (c) on the side of the accelerator repeats a cycle of an incidence, an acceleration, an emission, and a deceleration at a predetermined cycle, but in the synchrotron beam extraction possible gate (d) and the respiration gate signal (b), an operation (phase control) of turning on or off a beam extraction is performed, so that a predetermined dose of the beam extraction (e) is applied to a diseased portion as a target only in the respiration phase suitable for the irradiation.

Next, an operation of the synchrotron will be described in detail. As described above, the operation of the synchrotron repeats a cycle of incidence, acceleration, extraction, and deceleration at a predetermined cycle. The cycle of the operation is dependent on an acceleration time, an extraction time, and operation energy of the synchrotron, and is substantially one second to several seconds. The particle beam is incident into the synchrotron from a device called an injector, and the acceleration of the synchrotron is started at a time point when a sufficient number of particles are accumulated. The preparation of an emitter is performed after the acceleration ends, and the beam extraction possible gate signal (d) is turned on by the control system of the synchrotron at a time point when the preparation is completed.

In the emission possible state, when the respiration gate is turned on, a beam is extracted from the synchrotron. A maximum time in which the synchrotron continuously extracts the beam is called a spill time. After the spill time, the beam extract possible gate is turned off, and the synchrotron device starts to prepare a deceleration. After the deceleration is completed, the incidence of the next operation cycle is performed.

A main object of the invention is to provide in advance a respiration timing (hereinafter, referred to as target respiration information) to the patient, as a cycle suitable for the operation cycle of the synchrotron, so that the patient breathe in synchronization with it. Next, a desirable characteristic upon creating the target respiration information will be described. Here, a case will be supposed in which the respiration cycle is longer than the operation cycle of the synchrotron. The general respiration cycle is equal to or more than 3 seconds, and the stable cycle thereof is before or after 4 seconds or longer than that in general. However, the operation cycle of the synchrotron is about 3 seconds, and may be equal to or less than 2 seconds when it is short. Accordingly, this assumption condition is satisfied in general, but the advantage of the invention is not dependent on this assumption condition.

It may be supposed that the target respiration cycle is an integer times the operation cycle of the synchrotron. In this case, it is possible to uniformly maintain the movement of the synchrotron for each respiration cycle. It is possible to obtain a higher efficiency when the integer is selected with a multiple as small as possible. That is, when a ratio between the operation cycle of the synchrotron and the respiration cycle is one to one, since it is possible to perform the irradiation for each respiration cycle, and to use the beam accelerated by the synchrotron every time, it is possible to realize an efficient operation. However, when the target respiration cycle is too far from the patient natural respiration, it is not desirable in that it is difficult to match the target respiration cycle with the patient.

Further, as described below, there is a case in which the time width of the respiration gate is important, and hence at this time, it is necessary to select the respiration cycle so as to easily obtain the desired respiration gate. When the respiration cycle is a half integer times (0.5 times, 1.5 times, or the like) the operation cycle of the synchrotron, a different operation is performed every other respiration cycle. In this case, the efficiency is slightly degraded, but even at this time, it is possible to obtain the advantage of the invention.

Next, it is desirable that the target respiration gate width is set to be equal to the spill time width of the synchrotron, or to be slightly longer than that in consideration of the respiration variation. In this case, it is possible to maximally use the particles accelerated by the synchrotron in each extraction. For example, in the case where the spill time width of the synchrotron is set to about 0.5 seconds, it is not difficult for the natural respiration of the patient to realize the respiration gate width.

FIG. 6 is a table showing a setting example of the target respiration gate width and the target respiration cycle for the operation parameter of two types of synchrotrons A and B, and shows a case in which one-time irradiation is performed for each respiration cycle. In FIG. 6, a "respiration gate efficiency" is calculated as a value obtained by dividing the time when the respiration gate is turned on by the respiration cycle. In addition, an "irradiation efficiency" indicates a ratio in which the beam of the synchrotron is able to be used on the assumption that the case, in which the irradiation is performed without any waste in the operation instead of the respiration synchronization, that is, all operation cycles of the synchrotron, is set to 1.

In the accelerator parameter A, a case is shown in which the operation cycle of the synchrotron is set to 2 seconds, and the spill time is set to 0.4 seconds. At this time, the target respiration cycle is set to 2 seconds, 4 seconds, 6 seconds, and 8 seconds, but since the cycle is too short in the case of 2 seconds, the case is excluded. If 0.4 seconds or more is able to be ensured for the target respiration gate, it is possible to perform the irradiation in all spill of the synchrotron. This degree of respiration gate can be easily realized in the patient by using the respiration navigation function. Among the case (1) to the case (3), 4 seconds of cycle of the case (1) is the most desirable in that the cycle is close to the stable respiration cycle, and the irradiation efficiency is higher than other cases.

In the accelerator parameter B, as in the case of the parameter A, the case (4) has the highest irradiation efficiency, but when it is thought that the respiration having 3.2 seconds of cycles is too short for the patient, it may be supposed that the case (5) is used.

As described above, on the basis of the operation cycle of the synchrotron, the respiration information informing device 33 informs the patient of the target respiration information having a predetermined cycle, and the patient is guided so as to consciously match the respiration state with the target respiration information.

Next, the setting of the phase between the respiration and the synchrotron will be described. In the phases of the operation patterns of the respiration waveform and the synchrotron, it is desirable to select the phase so that the emission possible gate of the synchrotron is located in the vicinity of the middle point where the amplitude of the respiration waveform is maximal, that is, the center of the valley of the respiration waveform. In the configuration of FIG. 1, the timing information (accelerator information) of the synchrotron is transmitted via the respiration synchronizing control computer 24, but the timing information may be directly transmitted from the synchrotron or the accelerator timing systems 11 and 12 to the respiration navigation device 31 through a hard wire. The target respiration pattern is created in advance to have the optimal phase.

In addition, in the mounting operation of the invention, when the information editing terminal 32 is provided with a function of freely selecting the phase, it is convenient in that the phase is minutely controlled in real time. For example, when the information of the target respiration pattern is delayed in the respiration navigation computer 31 so that the delay is set to a time (second), the treatment operator is able to appropriately correct the respiration timing informed to the patient.

So far, the method of performing one-time irradiation for each respiration has been described, but next, a method of performing two-time irradiation for each respiration will be described. In general, in order to perform n-time irradiation for each respiration, the length of the respiration gate requires at least (n−1)·Tsync+Tspill. In addition, Tsync indicates the one respiration cycle, and Tspill indicates the above-described spill time.

FIG. 7 is a table showing a setting example of the respiration gate width for the operation parameters A and B of two types of synchrotrons, and shows a case in which two-time irradiation is performed for each respiration cycle. In the case where the target respiration gate width is set to be equal to or more than 2.4 seconds, the case (7) has the highest irradiation efficiency, but the respiration in which 2.4 seconds of respiration gate is ensured in 4 seconds of respiration cycle may be difficult for the patient. When the threshold value of the respiration waveform is set to be high, the respiration gate can be prolonged, but it may be disadvantageous in that the precision is degraded. In such a case, the case (8) may be used. In the case of the acceleration parameter B, in the case (10), since the respiration in which 2.4 seconds of respiration gate is ensured in 3.2 seconds of respiration cycle is more difficult for the patient than the case (7), it is thought that the case (11) is realistic.

Likewise, in the target respiration information setting, the respiration cycle is set to be an integer times the operation cycle of the synchrotron having 3 seconds to 6 seconds in accordance with the above-described method, and the cycle close to the possible patient natural respiration cycle and the cycle which can be realized by the patient without any difficult may be selected. In the case where two-time irradiation is performed for each respiration cycle, the respiration gate is set so that the efficiency of the respiration gate is not more than about 50%. In the case where one-time irradiation is performed for each respiration cycle, it is not necessary to worry about the limitation of the respiration gate width. From these conditions, the respiration pattern having the best efficiency may be selected as the target respiration information.

Next, a sequence of creating the target respiration information will be described. The time point at which the target respiration information is created in the treatment flow may be appropriately set to the time point before acquiring the treatment plan information. In the particle beam treatment, the treatment plan is created before performing the irradiation treatment, but it is necessary to acquire the X-ray CT image of the diseased portion in the treatment plan. At this time, in the case where the irradiation treatment is performed on a portion such as a lung or a liver irradiated in synchronization with the respiration, it is necessary to acquire the treatment plan X-ray CT image in synchronization with the respiration in the same manner. For this reason, it is desirable that the target respiration information is created before acquiring the treatment plan X-ray CT image, and the respiration state is set to be the same as that of the irradiation treatment even in the X-ray CT scanning operation.

First, the respiration convenient for the patient is received, and the respiration waveform is acquired so as to obtain the average cycle. At this time, a portion to be used in the continuously acquired respiration waveform may be set so that the treatment operator is able to designate the portion by using the start time point and the end time point. Next, on the basis of the obtained average cycle, the treatment operator sets the target respiration cycle which is an integer times the operation cycle of the synchrotron.

Figure 4:
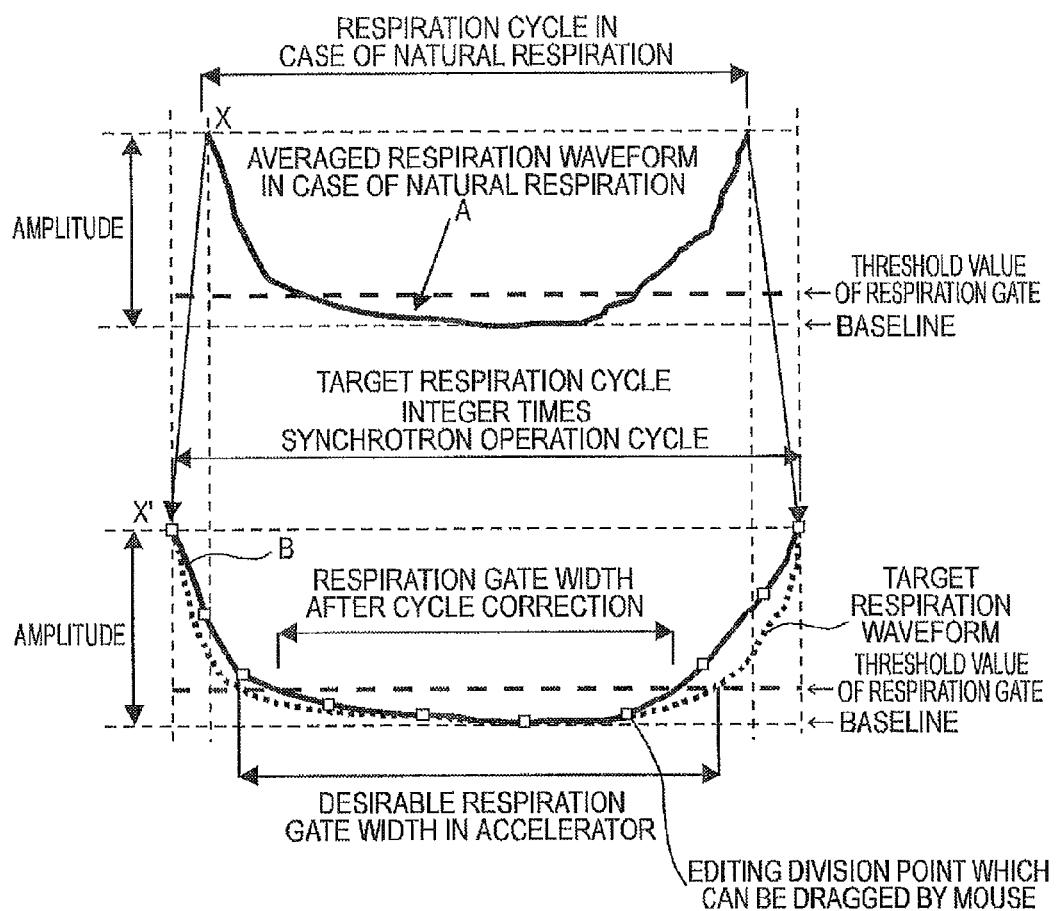
FIG. 4 is a diagram illustrating a sequence of creating target respiration information.

This cycle is informed the patient of and the patient is made to respire. The respiration waveform is acquired again, and the acquired respiration waveform is averaged as shown in A of FIG. 4. At the time of performing the average, since there is a difference in the respiration cycle in accordance with the different portion of the respiration waveform, as shown in the lower end B, the respiration waveform A of the upper end of the drawing is expanded or contracted (expanded in this case) so that the respiration cycle matches with the target respiration cycle, and the amplitude of the respiration waveform is averaged as depicted by the dotted line of the drawing. The respiration waveform for each cycle which is obtained and averaged in this manner is set to the target respiration waveform (information). At this time, in the same manner as described above, a portion to be used for the average in the continuously acquired respiration waveform may be set so that the portion is designated by the treatment operator by using the start time point and the end time point.

The target respiration information created as described above may be set to be edited in the information editing terminal and to be minutely controlled. For example, a function is provided in which the target respiration waveform is automatically divided by plural lines (editing division points), and the division points of the lines are dragged and edited by a mouse on the screen. When the editing function is provided, it is convenient that the respiration gate is set to the target value. In addition, it is convenient when there is provided a function of performing a control by multiplying the amplitude of the target respiration waveform by the coefficient or a function of moving up or down the baseline.

As another sequence of creating the target respiration information, the patient respiration is measured, and time-series information of the respiration is averaged for each cycle in accordance with the above-described method so as to create the standard respiration waveform. From the cycle of the target respiration waveform and the operation cycle of the synchrotron, the target respiration cycle having a good efficiency is set, and the cycle of the standard respiration waveform is expanded or contracted so as to be used as the target respiration information. In addition, the respiration gate width, the amplitude, or the like of the waveform may be edited in consideration of ease of the patient respiration as described above.

As described above, the phase may be set so that the center of the respiration gate overlaps with the spill center of the synchrotron. In addition, it may be supposed that the phase is set in consideration of the delay of the respiration due to the patient reaction time. As described above, when the information editing terminal 32 is provided with a function of controlling the phase of the target respiration information in real time, it is possible to control the phase on the site of treatment, and thus to recover the phase even when the phase deviates during the treatment.

In the case where two-time irradiation is performed for each respiration cycle, it is necessary to check that the target respiration gate width is ensured as well as the target respiration cycle. When the respiration gate width obtained by applying the threshold value to the target respiration waveform created as described above is sufficiently long, it is possible to directly use the target respiration waveform. When the length of the respiration gate width is not sufficient, the target respiration waveform may be edited by instructing the respiration gate width required for the information editing terminal of the target respiration waveform.

Next, a method of informing information such as an operation state of the synchrotron, respiration state information, and target respiration information using the respiration information informing device will be described with reference to FIG. 5.

As information informed to the patient, it may be supposed that only the timing of exhalation, inhalation, or the like is substantially informed in real time instead of the respiration waveform, but it is desirable to inform information including amplitude information of the respiration, that is, both the target value and the current value in real time in that the patient respiration becomes stable.

In some patients, there is a case in which the respiration synchronizing irradiation is difficult due to the small or unstable amplitude of the respiration waveform, but when the target value and the current value of the respiration amplitude are informed to the patient, the patient is able to control his/her respiration to be in a state suitable for the irradiation. In addition, when the respiration waveform is informed as a time graph, and displayed so that the patient easily distinguishes the past and future, the patient is able to easily estimate the respiration waveform, and hence the target respiration information is easily matched.

Figure 5:
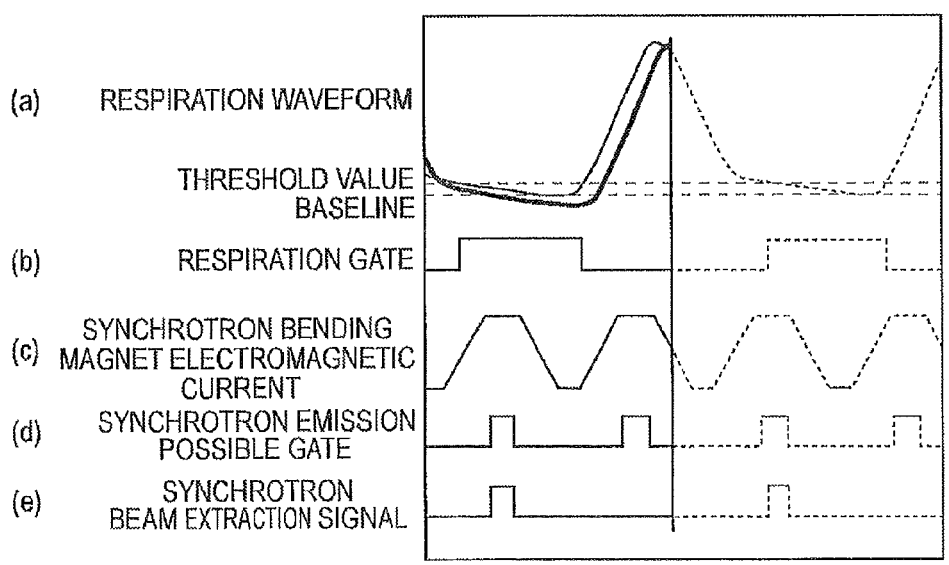
FIG. 5 is a diagram showing an example of a display screen of a respiration information informing device.

FIG. 5 shows an example of a display screen for giving such information, and FIGS. 5(a) to 5(e) are the same as those of FIG. 3. In the drawing, the waveform is scrolled from the left to the right in real time. The left side of the center of the screen indicates the past record, and the right side thereof indicates the future waveform. The bold respiration waveform indicates the patient actual waveform, and the thin respiration waveform indicates the target respiration information.

As a visual display method, a method may be supposed which installs a liquid crystal display screen at a position which can be seen by the patient lying on the treatment table, projects an image on a wall surface of the treatment apparatus or a wall surface of the treatment room, or uses a head mount display.

As visually displayed information, it may be supposed that the respiration waveform or the operation pattern of the synchrotron is displayed as time-series pattern information so as to flow from the left to the right of the screen. A display using the time-series data curve such as the respiration waveform or a display using an object position variation in which the target respiration information and the patient actual respiration state are displayed as a bar may be supposed. Various similar methods may be supposed in which the same information is displayed as a brightness variation, a color variation, a dimension variation, or a shape variation of an object.

In addition, as a method of informing information instead of a visual informing method, a method may be supposed in which the timing of exhalation or inhalation is instructed by voice guidance by installing a speaker at a position close to the patient. In the same manner, a method may be supposed in which the respiration cycle is set to be an integer times a beat (a time interval of a beat) of music by using an existing digital processing technology. In the case of using a tone of a sound instead of music, a method may be supposed in which the respiration cycle is instructed to the patient by using a variation in pitch of a tune, a variation in dynamics, a variation in tone, or the like. At this time, the amplitude of the respiration waveform may be displayed by using the dynamics of a sound. In addition, in addition to the senses of vision and hearing, a method may be supposed in which a vibrating device is gripped by the patient, and a vibration of the vibrating device coming into directly contact with the patient is controlled so as to use the respiration cycle for the patient. The acoustic informing method may be used together with the visual informing method.

As the operation information of the synchrotron which is information informed to the patient, an excitation current of a main bending magnet electromagnet of the synchrotron is preferable. In addition, there is a master signal showing the initial operation pattern of the synchrotron. In addition to the master signal, it may be supposed that timing signals corresponding to particular events in the operation cycle of the synchrotron such as the incidence start, the acceleration start, the acceleration end, and the emission possible period start is used as information informed to the patient, but since all the timing signals can be generated by making an appropriate delay from the master signal on the basis of the operation pattern of the synchrotron, basically the timing signals are equal to the master signal.

When the operation information of the synchrotron is informed to the patient, the patient is able to understand the operation state of the synchrotron, and the operation information is used as assistance information so as to be close to the target respiration pattern. The transmission of the operation information of the synchrotron may be input to the respiration navigation device via the respiration synchronizing signal generating device, but a method may be supposed in which the operation information is directly distributed from the acceleration timing system and the synchrotron bending magnet electromagnetic power supply so as to be transmitted to the respiration navigation device.

When the above-described target respiration information is stored in a transportable device such as a notebook PC capable of performing a storage and a display or a storage medium such as a CD-ROM, the patient is able to use in advance the target respiration information as the respiration training through a PC in a house, a hospital room, or the like. Accordingly, the patient is able to more faithfully make his/her respiration to be close to the target respiration pattern. Since it is difficult to use the respiration measurement device during the training, only the target respiration information may be informed to the patient.

The invention claimed is:

1. A respiration navigation apparatus used for a particle beam treatment apparatus including an accelerator operated on the basis of predetermined operation timing information, the respiration navigation apparatus comprising:
   a respiration navigation computer which stores target respiration information having a cycle set in advance on the basis of the operation timing information, and
   a respiration information informing device which informs a patient of distinct past and future portions of a respiration waveform obtained by quantifying information, involved with a respiration amplitude of the target respiration information, in time series.

2. The respiration navigation apparatus according to claim 1, further comprising:
   a patient respiration measurement device which measures a patient respiration state,
   wherein the respiration information informing device informs the patient of patient respiration state information, measured by the patient respiration measurement device, in real time.

3. The respiration navigation apparatus according to claim 1,
   wherein operation state information of the accelerator is input to the respiration navigation computer, and
   wherein the respiration information informing device informs the patient of the operation state information in real time.

4. The respiration navigation apparatus according to claim 3,
   wherein the respiration information informing device informs the operation state information including a waveform of a current supplied to an electromagnet of the accelerator or an emission beam signal when a beam is actually emitted.

5. The respiration navigation apparatus according to claim 1, further comprising:
   an information editing terminal which is able to control a phase of the target respiration information, input from the respiration navigation computer, in real time.

6. A particle beam treatment apparatus comprising:
   a particle beam generating device which includes an accelerator operated on the basis of predetermined operation timing information and generates a particle beam;
   a patient respiration measurement device which measures a patient respiration state;
   a respiration synchronizing device which allows a patient to be irradiated with the particle beam on the basis of the patient respiration state information measured by the patient respiration measurement device;
   a respiration navigation computer which stores target respiration information having a cycle set in advance on the basis of the operation timing information; and
   a respiration information informing device which informs the patient of distinct past and future portions of a respiration waveform obtained by quantifying information, involved with a respiration amplitude of the target respiration information, in time series.

7. The particle beam treatment apparatus according to claim 6, wherein the respiration information informing device informs the patient of patient respiration state information measured by the patient respiration measurement device in real time.

8. The particle beam treatment apparatus according to claim 6,
wherein operation state information of the accelerator is input to the respiration navigation computer, and
wherein the respiration information informing device informs the patient of the operation state information in real time.

9. The particle beam treatment apparatus according to claim 8,
wherein the respiration information informing device informs the operation state information including a waveform of a current supplied to an electromagnet of the accelerator or an emission beam signal when a beam is actually emitted.

10. The particle beam treatment apparatus according to claim 6, further comprising:
an information editing terminal which is able to control a phase of the target respiration information, input from the respiration navigation computer, in real time.

* * * * *